(12) United States Patent
Lee

(10) Patent No.: US 6,245,018 B1
(45) Date of Patent: Jun. 12, 2001

(54) ULTRASONIC COLOR DOPPLER IMAGING SYSTEM CAPABLE OF DISCRIMINATING ARTERY AND VEIN

(75) Inventor: Min Hwa Lee, Seoul (KR)

(73) Assignee: Medison Co., Ltd., Hongchun-Kun (KR)

( * ) Notice: Subject to any disclaimer, the term of this patent is extended or adjusted under 35 U.S.C. 154(b) by 0 days.

(21) Appl. No.: 09/212,158

(22) Filed: Dec. 15, 1998

(30) Foreign Application Priority Data

Dec. 15, 1997 (KR) .................................................. 97-68857

(51) Int. Cl.[7] ....................................................... A61B 8/00
(52) U.S. Cl. .............................................................. 600/454
(58) Field of Search ................................... 600/457, 454, 600/465, 455, 451, 443

(56) References Cited

U.S. PATENT DOCUMENTS

| | | | | |
|---|---|---|---|---|
| 5,123,417 | * | 6/1992 | Walker et al. | 600/465 |
| 5,148,808 | * | 9/1992 | Satake | 600/451 |
| 5,156,152 | * | 10/1992 | Yamazaki et al. | 600/447 |
| 5,441,052 | * | 8/1995 | Miyajima | 600/455 |
| 5,623,930 | * | 4/1997 | Wright et al. | 600/465 |
| 5,628,322 | * | 5/1997 | Mine | 600/437 |

FOREIGN PATENT DOCUMENTS

| | | |
|---|---|---|
| 3191951 | 12/1989 | (JP) . |
| 2215446 | 8/1990 | (JP) . |
| 2268748 | 11/1990 | (JP) . |
| 5200025 | 1/1992 | (JP) . |
| 4-13103 | 2/1992 | (JP) . |
| 5095947 | 4/1993 | (JP) . |
| 7-23951 | 1/1995 | (JP) . |
| 9135830 | 5/1997 | (JP) . |

OTHER PUBLICATIONS

Katsuhide Endo, M.D. "An assessment of fetoplacental circulation by Doppler flow velocity waveforms", Department of Obstetrics and Gynecology, School of Medicine, Keio Univeristy, 1989, pp. 433–443, 475.

* cited by examiner

Primary Examiner—Marvin M. Lateef
Assistant Examiner—Martin Patel
(74) Attorney, Agent, or Firm—F. Chau & Associates, LLP

(57) ABSTRACT

An ultrasonic color Doppler imaging system capable of discriminating an artery and a vein discriminates types of blood vessels such as the artery and the vein, and discriminatively displays the discriminated result on a display. The blood vessel types of the artery and the vein are determined using blood stream information according to a temporal change of a blood stream velocity pattern, and a different color is displayed according to the determined blood vessel type. Also, the brighter or darker color is displayed according to the blood stream velocity flowing in the blood vessel, to thereby provide accurate blood stream information.

14 Claims, 3 Drawing Sheets

ULTRASONIC COLOR DOPPLER IMAGING SYSTEM CAPABLE OF DISCRIMINATING ARTERY AND VEIN

BACKGROUND OF THE INVENTION

1. Field of the Invention

The present invention relates to an ultrasonic color Doppler imaging system, and more particularly, to an ultrasonic color Doppler imaging system capable of discriminating an artery and a vein, in which a blood stream velocity detected during imaging of the blood stream is used to discern the type of a blood vessel such as an artery or a vein and display the discerned result.

2. Description of the Related Art

Recently, an ultrasonic diagnostic system is widely used in a general medical treatment field. The ultrasonic diagnostic system uses phenomena such as reflection, scattering and absorption occurring when an ultrasonic wave passes through a living organism texture. The scattered signal contains acousto-impedance difference information at the boundary where a scattering occurs or movement velocity information of a scattering body. A dispersion intensity corresponding to an intensity of an actual reception signal reflects an acousto-impedance difference, and a frequency shift amount due to a Doppler effect reflects a movement velocity, more specifically, a velocity component with respect to a travelling direction of an ultrasonic beam.

A Doppler diagnostic apparatus being a kind of an ultrasonic diagnostic apparatus displays in an image form a frequency shift amount together with a signal dispersion intensity, to thereby estimate the dynamic functions in the living body. In particular, the color Doppler imaging system capable of displaying an ultrasonic color image demodulates a received signal and then digitizes the demodulated signal to process the digitized result, by which a blood stream flowing in the heart or in a main blood vessel can be described as a two-dimensional (2D) image in a real time. The color Doppler imaging system can display both tomogram and blood stream information. To identify the tomogram and the blood stream information from each other, the color Doppler imaging system displays the tomogram in monochrome and the blood stream information in colors.

When a blood stream distribution is displayed in the above color Doppler imaging system, the blood stream flowing toward the travelling direction of an ultrasonic beam emitted from a transducer is displayed as a blue color and that flowing toward the counter-direction thereof is displayed as a red color. The color Doppler imaging system displays the brightness of a color differently according to the blood stream velocity, in which the faster the brighter, and the slower the darker.

However, the above method in which the blood stream information is displayed according to the travelling direction of the ultrasonic beam can discriminate only the direction and velocity of the blood stream, but cannot discriminate whether the blood vessel of the blood stream is either a vein or an artery.

SUMMARY OF THE INVENTION

To solve the above problems, it is an object of the present invention to provide an ultrasonic Doppler color imaging system capable of discriminating an artery and a vein in which the type of a blood vessel such as the artery or the vein is discriminated using a temporal change in the velocity pattern of a blood stream, and the blood stream is displayed as a predetermined color according to the type of the discriminated blood vessel.

To accomplish the above object of the present invention, there is provided an ultrasonic color Doppler imaging system capable of discriminating an artery and a vein, the ultrasonic color Doppler imaging system comprising:

a first detector for detecting blood stream information from an ultrasonic echo signal reflected from an object; a second detector for detecting whether a blood vessel is an artery or a vein using the detected blood stream information; and a discriminative display portion for discriminatively displaying an ultrasonic color Doppler image on a display so that the type of the detected blood vessel is discriminated from each other as a color.

BRIEF DESCRIPTION OF THE DRAWINGS

The above object and other advantages of the present invention will become more apparent by describing the preferred embodiment thereof in more detail with reference to the accompanying drawings in which.

DETAILED DESCRIPTION OF THE PREFERRED EMBODIMENT

A preferred embodiment of the present invention will be described with reference to the accompanying drawings.

Figure 1A:
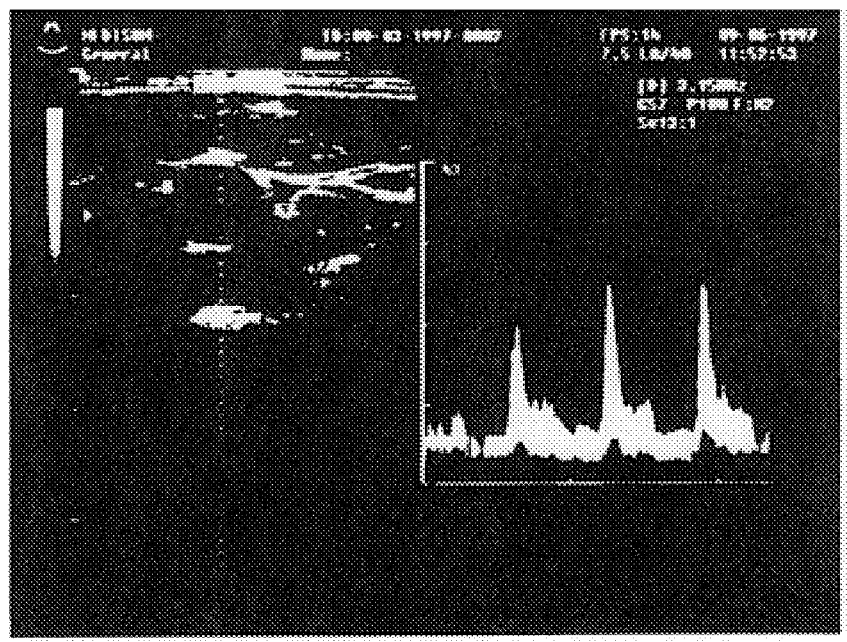
FIGS. 1A and 1B show the velocity patterns of blood streams in an artery and a vein, respectively.
Figure 1B:
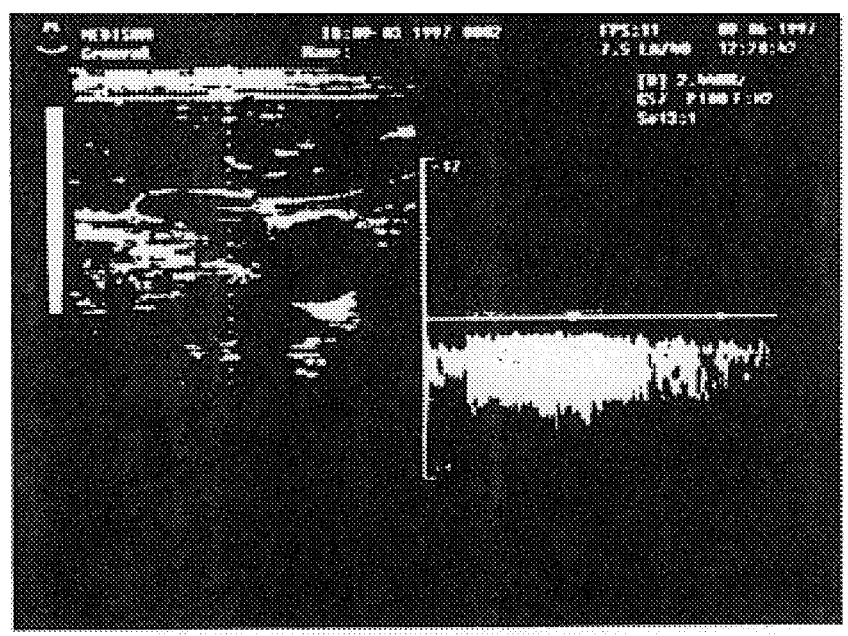

FIGS. 1A and 1B show spectral blood stream velocity patterns according to the period of a heartbeat, in which the vertical axis represents a blood stream velocity and the horizontal axis represents a time. Here, FIGS. 1A and 1B show changes in the velocity patterns of the blood stream in the artery and the vein.

A pulsatility index (PI) and a resistivity index (RI) are used as parameters in order to quantify the results obtained from observation of a blood stream at one spot in a human body for a certain time. The PI is obtained by subtracting a minimum value (min) from a maximum value (max) of the blood stream velocity according to a heartbeat period, and then dividing the resultant value by an average value (avr) of the blood stream velocity. The RI is obtained by subtracting a minimum value (min) from a maximum value (max) of the blood stream velocity according to the heartbeat period, and then dividing the resultant value by the maximum value (max). The PI and the RI are expressed as the following equations (1) and (2).

$$PI = \frac{(\max - \min)}{avr} \quad (1)$$

$$RI = \frac{(\max - \min)}{\max} \quad (2)$$

As shown in FIG. 1A, the artery has a large difference between the maximum value (max) and the minimum value (min) of the blood stream velocity according to a heartbeat period is large. However, as shown in FIG. 1B, the vein has little difference between the maximum value (max) and the minimum value (min) of the blood stream velocity according to a heartbeat period. Thus, in case of the artery, the values of the PI and the RI are large, and in case of the vein, those of the PI and the RI are close to "zero." The present invention uses the above features to discriminate the artery and the vein.

Figure 2:
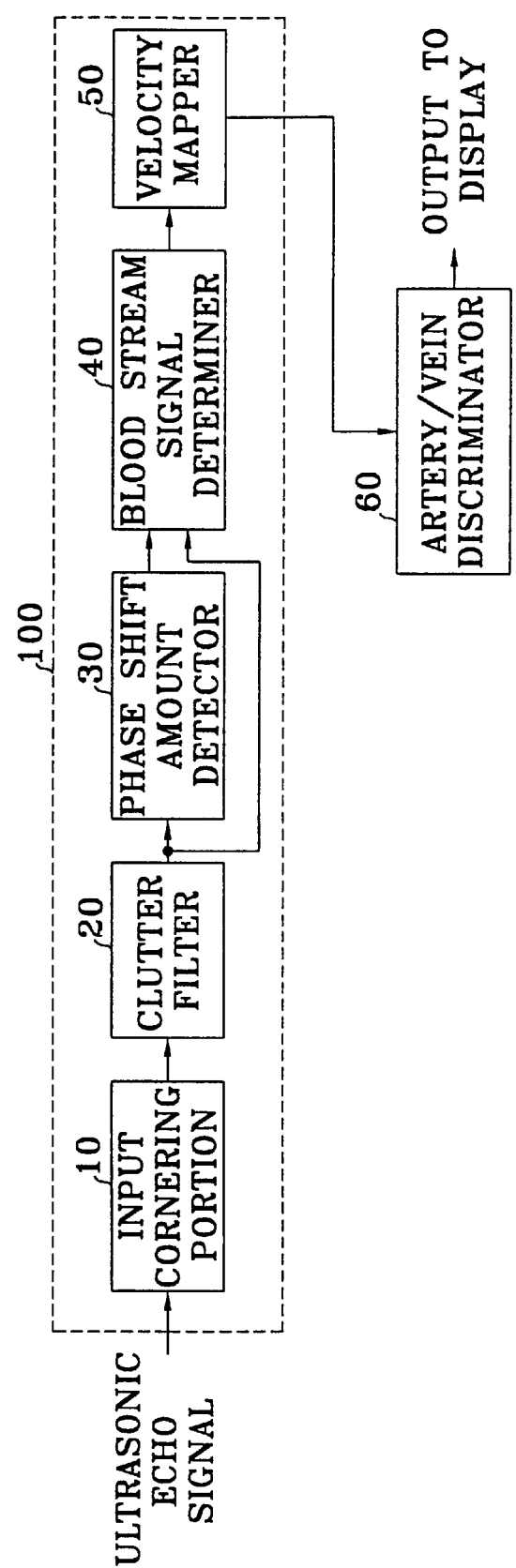
FIG. 2 is a block diagram showing an ultrasonic color Doppler imaging system according to the present invention.

FIG. 2 is a block diagram showing an ultrasonic color Doppler imaging system according to the present invention. The system shown in FIG. 2 includes a blood stream velocity pattern detector 100 for detecting a pattern of a blood stream from an ultrasonic echo signal, and an artery/vein discriminator 60 for discriminating the type of a blood vessel using a temporal change of the detected blood stream velocity pattern. The blood stream velocity pattern detector 100 includes an input cornering portion 10 for collecting ultrasonic echo signals corresponding to an identical point in time, and a clutter filter 20 for removing a signal other than a blood stream signal, that is, a signal reflected from tissues or musculus from a signal output from the input cornering portion 10. The blood stream velocity pattern detector 100 includes a phase shift amount detector 30 for detecting an average of a phase shift amount with respect to the output signal of the clutter filter portion 20, and a blood stream signal determiner 40 for determining whether the output signal of the clutter filter portion 20 is a blood stream signal and outputting the average of the phase shift amount detected in the phase shift amount detector 30. Also, a velocity mapper 50 in the blood stream velocity pattern detector 100 converts the average of the phase shift amount output from the blood stream signal determiner 40 into velocity data and outputs the converted result to the artery/vein discriminator 60. The artery/vein discriminator 60 discriminates whether a blood vessel is an artery or a vein according to a temporal change of the blood stream velocity pattern, and maps an artery as a first color and a vein as a second color according to the discriminated result, and outputs the mapped result to a display.

The operation of the FIG. 2 system having the above structure will be described below with reference to FIG. 3.

A general transducer transmits an ultrasonic pulse at a certain interval toward an object several times repetitively, and receives an ultrasonic echo signal returning from the object. Data obtained at an identical point in time is required to calculate a blood stream velocity with respect to each pixel. The input cornering portion 10 collects the signals received with transducer elements of a probe at an identical point in time in order to represent a pixel during reception of an ultrasonic echo signal. That is, an alignment direction of the ultrasonic echo signal is rotated by 90° and the signals received at an identical point in time are collected. The clutter filter 20 removes a low frequency Doppler signal reflected from tissues or musculus other than a blood stream signal from the output signal of the input cornering portion 10, and then outputs the resultant signal to the phase shift amount detector 30 and the blood stream signal determiner 40. Here, the clutter filter 20 performs a high pass filtering with respect to the signal supplied from the input cornering portion 10 to remove a low frequency Doppler signal therefrom. The phase shift amount detector 30 detects an average of the phase shift amount with respect to the output signal of the clutter filter 20 and outputs an average of the detected phase shift amount to the blood stream signal determiner 40. The blood stream signal determiner 40 compares the output signal of the clutter filter 20 with a predetermined threshold value to judge whether the output signal is a blood stream signal. Here, the threshold value indicates a reference value for determining whether the output signal of the clutter filter 20 is a blood stream signal. The blood stream signal determiner 40 determines the output signal of the clutter filter 20 as noise if it is lower than the threshold value and as a blood stream signal if the former is higher than the latter. The blood stream signal determiner 40 provides the phase shift amount average applied from the phase shift amount detector 30 to the velocity mapper 50, if it determines the output signal of the clutter filter portion 20 as a blood stream signal. The velocity mapper 50 converts the phase shift amount of the blood stream signal applied from the blood stream signal determiner 40 into velocity data. In more detail, the velocity mapper 50 multiplies the phase shift amount $\Delta_\theta$ by a wavelength $\lambda_o$ corresponding to a center frequency of an ultrasonic signal emitted toward the object, and then divides the multiplied result by a result obtained by multiplying a period $T_{PRF}$ of the ultrasonic signal by $2\pi$, to thereby obtain an approximate blood stream velocity $v_o$, whish is defined as the following equation (3).

$$v_o = \frac{\Delta_\theta \lambda_0}{2\pi T_{PRF}} \quad (3)$$

The artery/vein discriminator 60 discriminates the types of the blood vessels such as an artery and a vein using the blood stream velocity obtained in the velocity mapper 50 and maps the discriminated blood vessel type as a corresponding color to thereby output the mapped result to a display (not shown).

Figure 3:
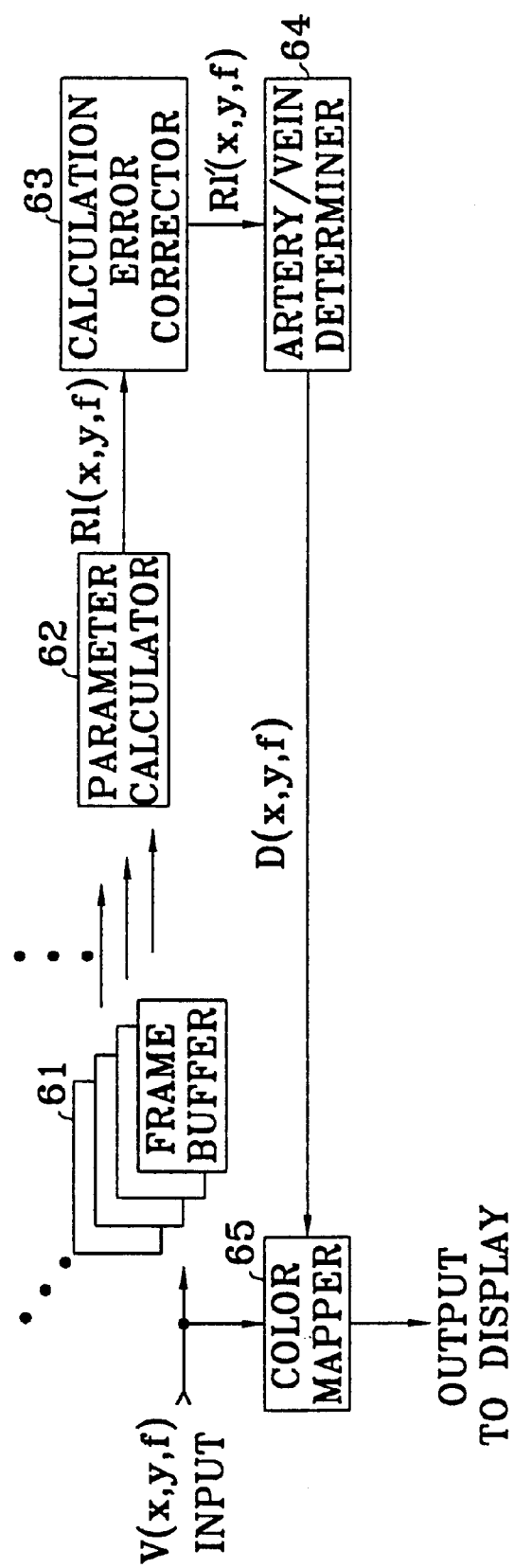
FIG. 3 is a detailed block diagram showing an artery/vein discriminator shown in FIG. 2.

FIG. 3 is a detailed block diagram showing the artery/vein discriminator shown in FIG. 2. The artery/vein discriminator 60 shown in FIG. 3 includes a frame buffer 61 for storing blood stream velocity data v(x,y,f) of each pixel in units of a frame which is supplied from the velocity mapper 50. The blood stream velocity data input to the frame buffer 61 is input to a color mapper 65. Also, the artery/vein discriminator 60 includes a parameter calculator 62 for calculating parameters such as a PI and a RI using the blood stream velocity data stored in the frame buffer 61, and a calculation error corrector 63 for correcting a calculation error occurring in the parameter calculator 62. The calculation error corrector 63 corrects a calculation error through a spatial operation between a parameter of each pixel calculated in the parameter calculator 62 and parameters of adjacent pixels. The artery/vein discriminator 60 of FIG. 3 also includes an artery/vein determiner 64 for determining whether a blood vessel of the blood stream measured according to the parameter of each pixel corrected in the calculation error corrector 63 is an artery or a vein, and the color mapper 65 for mapping a color of each pixel representing the blood stream according to the determined blood vessel type.

The artery/vein discriminator 60 of FIG. 3 having the above structure receives the blood stream velocity data v(x,y,f) of each pixel from the velocity mapper 50. Here, variables x and y represent horizontal and vertical positions of one pixel on one frame, and a variable f represents what order of frame it is. The input blood stream velocity data v(x,y,f) of each pixel is stored in the frame buffer 61 in units of a frame. The frame buffer 61 stores the blood stream velocity data of the pixels in a current frame and a predetermined number of previous frames. The parameter calculator 62 calculates the PI and the RI using the blood stream velocity data stored in the frame buffer 61. In this embodiment of the present invention, the blood vessel types of the artery and the vein are discriminated using the RI. The parameter calculator 62 calculates an approximate RI using the blood stream velocity data of the pixels in a number of frames which correspond to an identical position and are stored in the frame buffer 61. The parameter calculator 62 calculates a resistivity index function RI(x,y,f) by using the fastest blood stream velocity data as a maximum value 'max' and the slowest blood stream velocity data as a minimum value 'min' among the blood stream velocity data v(x,y,f-1), v(x,y,f-2), . . . , v(x,y,f-n) of the pixels corresponding to an identical position. The calculation error corrector 63 corrects a calculation error of the RI(x,y,f) with respect to the respective pixels calculated in the parameter calculator 62. The calculation error corrector 63 corrects the calculation error of the RI(x,y,f) value of each pixel calculated in the parameter calculator 62 through a spatial operation between the resistivity indices of the adjacent pixels, and then outputs the corrected result to the artery/vein determiner 64. Here, the spatial operation is performed via a spatial average, however, a two-dimensional median filter or a variety of heuristic operations can be used as required. The artery/vein determiner 64 compares the resistivity index RI'(x,y,f) of each pixel which has been corrected via the spatial operation in the calculation error corrector 63 with a predetermined reference value in order to determine a blood vessel type. When a PI is used to discriminate a blood vessel type, a particular reference value is used so that an artery and a vein can be discriminated based on a pulsatility index. The artery/vein determiner 64 determines a blood vessel as an artery if the resistivity index RI'(x,y,f) of each pixel corrected in the calculation error corrector 63 is larger than a predetermined reference value, and as a vein if the former is smaller than the latter. The artery/vein determiner 64 outputs the determination result D(x,y,f) of the blood vessel type with respect to each pixel to the color mapper 65. The color mapper 65 determines which color will be mapped to the pixel representing the blood stream velocity data v(x,y,f) supplied from the velocity mapper 50, according to the determination result D(x,y,f) of the artery/vein determiner 64. The color mapper 65 maps the pixel determined as an artery in the artery/vein determiner 64 into red, and the pixel determined as a vein into blue, and outputs the mapped result to a display. In the color mapper 65, the faster, the lighter the pixel is mapped into red or blue, while the slower the darker red or blue, to then output the mapped result to a display. The color mapped blood stream is processed properly and displayed on the display.

The above method for discriminating an artery and a vein using the calculated values is described in only one embodiment of the present invention. It is apparent to a person who has an ordinary skill in the art, that an artery and a vein can be discriminated by an alternative method using a blood stream velocity pattern being different from the above method.

As described above, the color Doppler imaging system capable of discriminating an artery and a vein according to the present invention determines a blood vessel type of the artery and the vein using a blood stream velocity, and discriminatively displays the result with a respectively different color according to the discriminated blood vessel type. Also, the present invention can display the discriminated result with a brighter or darker color according to the travelling velocity of the blood stream, to thereby provide accurate blood stream information.

While only certain embodiments of the invention have been specifically described herein, it will be apparent that numerous modifications may be made thereto without departing from the spirit and scope of the invention.

What is claimed is:

1. An ultrasonic color Doppler imaging system capable of discriminating an artery and a vein, the ultrasonic color Doppler imaging system comprising:

a first detector for detecting blood stream information from an ultrasonic echo signal reflected from an object;

a second detector for detecting whether a blood vessel is an artery or a vein using the detected blood stream information; and a discriminative display portion for discriminatively displaying an ultrasonic color Doppler image on a display so that the type of the detected blood vessel is discriminated from each other as a color.

2. The ultrasonic color Doppler imaging system according to claim 1, wherein said blood stream information is a blood stream velocity.

3. The ultrasonic color Doppler imaging system according to claim 1, wherein said first detector detects a blood stream velocity change pattern corresponding to each pixel position in the ultrasonic color Doppler image from the ultrasonic echo signal.

4. The ultrasonic color Doppler imaging system according to claim 3, wherein said second detector detects a blood vessel type according to the blood stream velocity change pattern detected in said first detector.

5. The ultrasonic color Doppler imaging system according to claim 4, wherein said second detector detects the blood vessel type based on the fact that a width of the blood stream velocity change differs from each other in the artery and the vein.

6. The ultrasonic color Doppler imaging system according to claim 5, wherein said second detector comprises:

a frame buffer for storing a blood stream velocity of pixels in a plurality of frames detected in said first detector;

a parameter calculator for calculating a parameter capable of discriminating an artery and a vein using the blood stream velocity of each pixel in the plurality of frames which corresponds to an identical position and is stored in said frame buffer; and an artery/vein determiner for comparing the parameter calculated in said parameter calculator with a predetermined reference parameter and determining whether said each pixel belongs to either the artery or the vein.

7. The ultrasonic color Doppler imaging system according to claim 6, wherein said parameter is a resistivity index RI, which is defined as $$RI = \frac{(\max - \min)}{\max}$$

wherein the max represents the fastest blood stream velocity among the blood stream velocity of pixels corresponding to an identical position, and the min represents the slowest blood stream velocity among the blood stream velocity of each pixel corresponding to an identical position.

8. The ultrasonic color Doppler imaging system according to claim 6, wherein said parameter is a pulsatility index PI, which is defined as $$PI = \frac{(\max - \min)}{avr}$$

wherein the max represents the fastest blood stream velocity among the blood stream velocity values of the pixels corresponding to an identical position, and the min represents the slowest blood stream velocity among the blood stream velocity values of the pixels corresponding to an identical position, and the avr represents an average blood stream velocity.

9. The ultrasonic color Doppler imaging system according to claim 6, wherein said artery/vein determiner determines the blood vessel as an artery if the parameter of each pixel calculated in said parameter calculator is larger than a predetermined parameter, and as a vein if the former is smaller than the latter.

10. The ultrasonic color Doppler imaging system according to claim 9, further comprising a calculation error corrector for correcting a calculation error of the parameter of each pixel calculated in the parameter calculator through a spatial operation between the parameters of the adjacent pixels.

11. The ultrasonic color Doppler imaging system according to claim 10, wherein said discriminative display portion comprises a color mapping portion for determining a color of the pixel representing the blood stream velocity detected in said first detector according to the determination result of said artery/vein determiner and mapping the determined result into a corresponding color.

12. The ultrasonic color Doppler imaging system according to claim 11, wherein said color mapping portion maps a pixel determined as an artery in said artery/vein determiner into red, and that determined as a vein into blue.

13. The ultrasonic color Doppler imaging system according to claim 12, wherein said color mapping portion maps the color of the pixel so that the brightness of the color is varied according to the blood stream velocity detected in said first detector.

14. The ultrasonic color Doppler imaging system according to claim 13, wherein said color mapping portion maps the pixel into a brighter color as the blood stream velocity is faster, and the darker color as the blood stream velocity is slower.

* * * * *